United States Patent
Cordier et al.

[11] Patent Number: 6,005,145
[45] Date of Patent: Dec. 21, 1999

[54] METALLIC COMPOUNDS USEFUL AS CATALYSTS

[75] Inventors: Georges Cordier, Francheville, France; Jean-Michel Popa, Campinas, Spain

[73] Assignee: Rhone-Poulenc Fiber and Resin Intermediates, Courbevoie Cedex, France

[21] Appl. No.: 09/043,375

[22] PCT Filed: Sep. 12, 1996

[86] PCT No.: PCT/FR96/01406

§ 371 Date: Aug. 3, 1998

§ 102(e) Date: Aug. 3, 1998

[87] PCT Pub. No.: WO97/10052

PCT Pub. Date: Mar. 20, 1997

[30] Foreign Application Priority Data

Sep. 15, 1995 [FR] France ................................. 95/11064

[51] Int. Cl.⁶ .................................................. C07C 209/00
[52] U.S. Cl. ............................. 564/490; 564/491; 564/492
[58] Field of Search ................................... 564/490, 491, 564/492

[56] References Cited

U.S. PATENT DOCUMENTS 5,232,887  8/1993  Blaise et al. .

FOREIGN PATENT DOCUMENTS

| 0 566 197 | 10/1993 | European Pat. Off. . |
| 2 091 785 | 1/1972 | France . |
| 1 336 865 | 11/1973 | United Kingdom . |
| 94 14700 | 7/1994 | WIPO . |

*Primary Examiner*—Samuel Barts
*Attorney, Agent, or Firm*—Burns, Doane, Swecker & Mathis, L.L.P.

[57] ABSTRACT

The present invention relates to new metal compounds, to a process for the preparation of these metal compounds and to their use as catalysts.

The new metal compounds according to the invention have, when they are used as catalysts, in particular as hydrogenation catalysts, an efficiency of the same order as that obtained with Raney nickel or cobalt.

These metal compounds are more precisely compounds containing one or a number of divalent metals at least partially in the reduced state, bulked by a phase comprising one or a number of doping metals chosen from chromium, molybdenum, iron, manganese, titanium, vanadium, gallium, indium, bismuth, yttrium, cerium, lanthanum and the other trivalent lanthanides, in the form of oxides.

12 Claims, No Drawings

METALLIC COMPOUNDS USEFUL AS CATALYSTS

This application is a 371 of PCT/FR96/01406 filed Sep. 12, 1996.

The present invention relates to new metal compounds, to a process for the preparation of these metal compounds and to their use as catalysts.

Hydrogenation catalysts based on nickel or on cobalt represent an important class among the many metal compounds used in particular as catalysts in various chemical reactions. These hydrogenation catalysts based on nickel or on cobalt are in particular Raney nickel and Raney cobalt, which are widely used in industry in many hydrogenation reactions.

Catalysts of this type, which are very efficient and which possess very broad fields of application, nevertheless exhibit a number of disadvantages and a number of limitations of use.

First of all, they are prepared by attack, using a strong base, on an alloy containing nickel or cobalt and a high proportion of aluminium.

Such a preparation therefore necessarily involves the generation of large amounts of basic aqueous effluents containing aluminates, the treatment of which effluents is essential.

Another limitation on the use of Raney nickel and cobalt is due to the fact that their reduced form is pyrophoric; it must be handled with care and can only be used protected, either in the form of a suspension or liquid or in the form coated in a protective solid. Use in a stationary bed on an industrial scale is thereby rendered difficult.

Finally, a progressive deactivation of Raney nickel or cobalt is observed, whereas no efficient means of regeneration is known. One of the hypotheses which seems accepted in explaining this deactivation, in particular in a medium containing water and more specifically in basic medium, is the progressive oxidation of the residual aluminium to aluminate, which coats the active surface of the nickel or of the cobalt.

Another form of metal catalyst has been used in order to overcome certain abovementioned disadvantages of Raney catalysts: the metals are deposited on a support. Thus, Patent EP-A-0,566,197 describes hydrogenation catalysts based on nickel and/or on cobalt deposited on a solid support, such as an aluminium silicate, an alumina or a silica, preferably with a cocatalyst, such as a non-acidic alkali metal or alkaline-earth metal oxide or salt.

In this type of catalyst, the homogeneity of the distribution of the active metal in the solid support is not always very good. In addition, the presence of a support can, in certain cases, limit the activity of the catalyst and, in any event, dilutes the active metal phase.

Thus, in Patent EP-A-0,566,197, the Examples show that the active metal content of the supported catalysts does not exceed 20% and is often 5%. Finally, the method of deposition of the active metal, by impregnation of the support, can result in partial dissolution of the active metal in the reaction mixture, when the catalyst is used.

Patent FR-A-2,091,785 describes catalysts composed of active metal oxides, of active metals or of active metal oxides and of support materials, comprising magnesium, nickel, cobalt; divalent copper, zinc, manganese and/or iron and trivalent aluminium, chromium and/or iron. The proportion of divalent and trivalent metals in these catalysts is, in practice, 6 atoms of divalent metals per 2 atoms of trivalent metals.

These catalysts contain essentially aluminium as trivalent metal and magnesium, nickel and cobalt, sometimes in combination with other metals, as divalent metals. They can be used for the dehydrogenation of secondary alcohols or of monoolefins, isomerization or dealkylation reactions or for the hydrogenation of nitro compounds.

The new metal compounds according to the invention possess, when they are used as catalysts, in particular as hydrogenation catalysts, an efficiency of the same order as that obtained with Raney nickel or cobalt, while not exhibiting the disadvantages indicated above, in particular as regards their deactivation and their regeneration.

In addition, as they do not contain a support, they are composed virtually only of active compounds.

These metal compounds are more precisely compounds containing one or a number of divalent metals, at least partially in the reduced state, bulked by a phase comprising one or a number of doping metals chosen from chromium, molybdenum, iron, manganese, titanium, vanadium, gallium, indium, bismuth, yttrium, cerium, lanthanum and the other trivalent lanthanides, in the form of oxides.

The metals present in the form of oxides are known as doping metals in the present text, because they are necessary to the divalent metals for optimum exertion of their catalytic activity, in particular because they confer a sufficient specific surface on the combination.

The divalent metals are preferably nickel or cobalt.

In general, at least 20% of their atoms are in the reduced state, that is to say in the 0 oxidation state. Preferably, at least 50% of the nickel or cobalt atoms are in the reduced state.

The divalent metals are provided in the form of particles having sizes generally lying between 1 and 20 nanometres. More specifically, the size of the divalent metal particles is from 3 to 5 nanometres. These particle sizes are measured by X-ray diffraction.

The divalent metal particles are homogeneously bulked with particles of at least one doping metal oxide in which the metal is chosen from the metals indicated above. The doping metal oxides exhibit particle sizes having the same order of magnitude as the divalent metal particles.

The specific surface of the metal compounds of the invention is generally between 20 $m^2/g$ and 150 $m^2/g$.

The doping metal/divalent metal molar ratio in the metal compounds of the invention is generally between 0.01 and 0.50.

This molar ratio is preferably from 0.05 to 0.30.

A portion of the divalent metals, nickel or cobalt, can be substituted by one or a number of other metals, such as, in particular, zinc, copper, silver, gold, ruthenium, platinum or palladium. These metals can represent, in moles per mole of nickel and/or cobalt, from 0% to 50%.

For the doping metal/divalent metal ratio defined above, these other metals optionally present are regarded as forming part of the combined divalent metals.

Likewise, the doping metal oxides can be partially replaced by aluminium oxide. This aluminium oxide can represent from 0% to 50% in moles of aluminium per mole of all the doping metals present.

The doping metals present in the form of oxides in the metal compounds of the invention are generally in the oxidation state 3 but can, for some of them, be at least partially in the oxidation states 4 or 5.

Another subject of the invention relates to the precursors of the metal compounds described above.

These precursors are provided as metal compounds containing one or a number of divalent metals in the form of oxides, bulked by a phase comprising one or a number of doping metals chosen from chromium, molybdenum, iron, manganese, titanium, vanadium, gallium, indium, bismuth, yttrium, cerium, lanthanum and the other trivalent lanthanides, in the form of oxides.

As indicated above for the metal compounds in which the divalent metal or metals are at least partially in the reduced state, from 0% to 50% in moles of these doping metal oxides can be replaced by aluminium oxide and from 0% to 50% in moles of the divalent metal oxide or oxides can be replaced by zinc, copper, silver, gold, ruthenium, platinum and/or palladium oxides.

The divalent metal oxides of these precursors, and the oxides of the majority of the metals which can replace a portion of the divalent metals, are easily reducible. The precursors make it possible to obtain, by reduction at relatively moderate temperature, the metal compounds of the invention.

This reduction can be carried out by heating under hydrogen. The reduction temperature is preferably between 200° C. and 500° C.

The hydrogen can be used under pressure or by sweeping.

The duration of the reduction can vary within very wide limits. By way of indication, it generally lies between a few minutes and 24 hours, most often between 1 and 10 hours.

The oxides of the doping metals, and in particular the optionally present aluminium oxide, are not reduced under the conditions for reduction of the divalent metals indicated above. The metal compounds of the invention therefore do not contain aluminium in the oxidation state 0, unlike Raney nickel or cobalt.

A process for the synthesis of the precursors of the metal compounds of the invention consists in preparing compounds having a structure belonging to the family of the lamellar double hydroxides (LDH) of hydrotalcite type and then calcining the said compounds of hydrotalcite type.

The hydrotalcites (or LDHs), thus called by extension of the name of the natural compound $Mg_6Al_2(OH)_{16}CO_3.4H_2O$, are compounds of general formula (I):

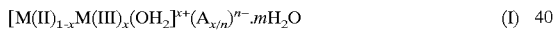

$$[M(II)_{1-x}M(III)_x(OH_2)]^{x+}(A_{x/n})^{n-}.mH_2O \qquad (I)$$

in which:

A represents an inorganic anion, such as carbonate, sulphate, nitrate, iodate, halide, vanadate, chromate, molybdate, aluminate, stannate, zincate, permanganate, cuprate, gallate, a heteropoly acid anion, a carboxylate anion or a mixture of a number of these anions, M(II) is a divalent metal, M(III) is a doping metal in the oxidation state 3, x represents a number from 0.01 to 0.33, n represents the valency of the A anion, m represents a variable number of molecules, depending on the method of preparation and on the drying conditions.

In the case of the LDHs resulting in the precursors of the metal compounds of the invention, M(II) at least partially represents Ni or Co and M(III) represents at least one doping metal in the oxidation state 3 chosen from chromium, molybdenum, iron, manganese, titanium, vanadium, gallium, indium, bismuth, yttrium, cerium, lanthanum and the other trivalent lanthanides.

The preferred hydrotalcites of formula (I) are those in which A represents a carbonate, nitrate, vanadate, chromate, molybdate, aluminate, stannate, zincate, permanganate, cuprate, gallate or carboxylate anion or a mixture of a number of these anions and x represents a number from 0.048 to 0.23.

The hydrotalcites of formula (I) are prepared by precipitation, during the mixing of aqueous solutions of inorganic compounds of the divalent metals and doping metals forming part of the composition of the said hydrotalcites and of a carbonate, in particular of an alkali metal carbonate.

The compounds which can be used are the water-soluble salts of the various M(II) and M(III) metals.

Mention may be made, as non-limiting examples of such compounds, of nickel nitrate, nickel chloride, nickel bromide, nickel iodide, nickel sulphate, cobalt bromide, cobalt chloride, cobalt iodide, cobalt nitrate, cobalt sulphate, copper acetate, copper chloride, copper nitrate, copper sulphate, silver fluoride, silver nitrate, zinc acetate, zinc bromide, zinc chloride, zinc formate, zinc nitrate, zinc sulphate, chromium chloride, chromium sulphate, chromium bromide, iron bromide, iron chloride, iron formate, iron nitrate, iron oxalate, iron sulphate, titanium chloride, titanium bromide, gallium bromide, gallium chloride, gallium nitrate, gallium sulphate, indium bromide, indium chloride, indium nitrate, indium sulphate, vanadium bromide, vanadium iodide, vanadyl sulphate, cerium acetate, cerium bromide, cerium iodide, cerium nitrate, lanthanum acetate, lanthanum bromide, lanthanum iodide, lanthanum nitrate, bismuth nitrate, molybdenum nitrate or manganese nitrate.

The dissolution of these compounds and the precipitation of the hydrotalcite of formula (I) are carried out at a temperature equal to or less than 100° C., The hydrotalcites of formula (I) in which A is an anion other than the carbonate anion can be obtained from the carbonate hydrotalcite prepared above, by exchange of the carbonate anions with other A anions in aqueous medium.

It is important to wash the hydrotalcite in order to remove as much as possible of the unprecipitated inorganic cations and anions arising from the compounds used. These ions are undesirable because they are capable, at least in certain cases, of promoting sintering of the divalent metal particles, resulting in an increase in the size of the latter and a decrease in the specific surface of the precursor and of the metal compound which will be prepared from the hydrotalcites.

The hydrotalcites thus obtained are then dried and then calcined in order to form the precursors of the metal compounds of the invention.

This calcination is generally carried out at a temperature of 250° C. to 600° C., generally while ventilating with air. The calcination temperature will be adjusted, in the defined region, to the nature of the doping metals and to the doping metal/divalent metal ratio.

The calcination time is highly variable. By way of indication, it most often lies between a few minutes and 24 hours.

The metal compounds according to the invention defined above can be used as catalysts in many reactions. Generally, they can be used in the reactions catalysed by Raney nickel or cobalt.

They are thus more specifically hydrogenation catalysts. They can therefore be used for the hydrogenation of various families of nitrogenous compounds, such as nitrites, imines, oximes, nitrogenous heterocycles, azo compounds or nitro compounds, of carbonyl compounds, such as sugars, for example, of compounds possessing carbon-carbon unsaturation, such as, for example, ethylenic compounds, of compounds possessing an aromatic ring, such as, for example, benzene or naphthalene compounds.

Preference is given, among substrates where hydrogenation using hydrogen can be catalysed by the metal compounds of the invention, to nitriles.

The metal compounds of the invention can be used in a process for the hydrogenation of aliphatic, cycloaliphatic, heterocyclic or aromatic mononitriles or dinitriles. Dinitriles represent a particularly advantageous family, due to the compounds in which they result.

These dinitriles are, more particularly but non-limitingly, the nitrile substrates of formula (II):

NC—R—CN     (II)

in which R represents a linear or branched alkylene or alkenylene group having from 1 to 12 carbon atoms or an unsubstituted or substituted arylene or aralkylene or aralkenylene group.

Use is preferably made of dinitriles of formula (II) in which R represents a linear or branched alkylene radical having from 1 to 6 carbon atoms.

Mention may be made, as examples of such dinitriles, of, in particular, adiponitrile, methylglutaronitrile, ethylsuccinonitrile, dimethylsuccinonitrile, malononitrile, succinonitrile and glutaronitrile and their mixtures, in particular the adiponitrile, methylglutaronitrile and ethylsuccinonitrile mixtures which arise from the same process for the synthesis of adiponitrile.

The hydrogenation reaction of the dinitriles is preferably carried out in the presence of a strong base. This strong base is preferably chosen from the following compounds: LiOH, NaOH, KOH, RbOH, CsOH and their mixtures.

In practice, use is most often made of NaOH and KOH, for a good performance/cost compromise, although RbOH and CsOH give even better results.

The hydrogenation reaction mixture is preferably liquid. It contains at least one solvent capable of dissolving the nitrile substrate to be hydrogenated, because this reaction takes place better when the said substrate is in solution.

According to an advantageous form of the hydrogenation process, use is made of an at least partially aqueous liquid reaction mixture. The water is generally present in an amount less than or equal to 50%, advantageously less than or equal to 20%, by weight with respect to the total reaction mixture. More preferentially still, the water content of the reaction mixture is between 0.1 and 15% by weight with respect to all the constituents of the said mixture.

At least one other solvent, of the alcohol and/or amide type, can be provided in complementing or in substituting for the water. The alcohols which are more particularly suitable are, for example, methanol, ethanol, propanol, isopropanol, butanol, glycols, such as ethylene and/or propylene glycol, polyols and/or mixtures of the said compounds.

In the case where the solvent is composed of an amide, it can, for example, be N-methylpyrrolidone or dimethylacetamide.

When it is employed with water, the solvent, preferably alcoholic, represents from 1% to 1000% by weight with respect to the weight of water and preferably from 2% to 300%.

According to another preferred characteristic of the hydrogenation, diamine, which is formed in the reaction, is incorporated in the reaction mixture. It is, for example, hexamethylenediamine when the nitrile substrate is adiponitrile.

The concentration of the targeted amine in the reaction mixture is advantageously between 50% and 99% by weight with respect to the whole of the solvent included in the said reaction mixture and, more preferentially still, is between 60% and 99% by weight.

The liquid-phase hydrogenation can be carried out noncontinuously (batchwise) on nitrile alone or optionally with other liquid compounds added, such as the diamine which is formed in the reaction and/or the solvent or solvents.

It can also be carried out with continuous introduction of the nitrile substrate.

When the reaction is carried out with nitrile and one or a number of solvents and/or diamine, introduction of the nitrile substrate, for example adiponitrile, into the reaction mixture is carried out while observing a concentration of between 0.001% and 30% by weight with respect to the total weight (w/w) of the liquid reaction mixture and preferably between 0.1% and 20% w/w.

The amount of base in the reaction mixture varies according to the nature of the reaction mixture.

When the reaction mixture contains only water and targeted amine as liquid solvent medium, the amount of base is advantageously greater than or equal to 0.1 mol/kg of catalyst, preferably between 0.1 and 2 mol/kg of catalyst and more preferentially still between 0.5 and 1.5 mol/kg of catalyst.

In the case where the reaction mixture comprises water and an alcohol and/or an amide, the amount of base is greater than or equal to 0.05 mol/kg of catalyst, preferably between 0.1 and 10.0 mol/kg and more preferentially still between 1.0 and 8.0 mol/kg.

The amount of catalyst is not critical because, depending on the embodiment of the process, it can be in an amount several times larger than the substrate to be hydrogenated, in particular when the latter is continuously introduced into the reaction mixture containing the catalyst. By way of indication, the catalyst can represent from 0.1% to 100% by weight of the weight of the liquid reaction mixture and most often from 1% to 50%.

Once the composition of the reaction mixture and the choice of the catalyst have been decided upon, these two components are mixed and this mixture is then heated to a reaction temperature less than or equal to 150° C., preferably less than or equal to 120° C. and more preferentially still less than or equal to 100° C.

In concrete terms, this temperature is between room temperature (approximately 20° C.) and 100° C.

Prior to, simultaneously with or subsequent to the heating, the reaction chamber is brought to the appropriate hydrogen pressure, that is to say, in practice, between 0.10 and 10 MPa.

The reaction time is variable, according to the reaction conditions and the catalyst.

In a batchwise operating mode, it can vary from a few minutes to a number of hours.

In a continuous operating mode, which is entirely conceivable for this type of reaction, the time is clearly not a set parameter.

It should be noted that the person skilled in the art can vary the sequence of the stages of the process, depending on the operating conditions. The order given above only corresponds to a preferred, but non-limiting, form of the hydrogenation process.

The other conditions which govern the hydrogenation (in continuous or batchwise mode) are a matter for conventional technical arrangements which are known per se.

By virtue of all the advantageous arrangements mentioned above, the metal compounds of the invention make possible the selective, rapid, convenient and economical hydrogenation of nitrile substrates to amines.

The hydrogenation of adiponitrile to hexamethylenediamine is particularly important, since this hydrogenated derivative is one of the basic monomers in the manufacture of polyamide 6,6.

The hydrogenation of dinitriles can also provide access to aminonitriles. Thus, it is possible to hydrogenate a single one of the two nitrile functional groups of adiponitrile to obtain aminocapronitrile. The latter compound can easily be converted, by cyclizing hydrolysis, to caprolactam, which is the starting material in another large-scale industrial synthesis of polyamide, namely polyamide 6.

The invention is illustrated by the following examples of the preparation of metal compounds of the invention and of the application of the latter in the hydrogenation of adiponitrile to hexamethylenediamine.

EXAMPLES

Examples of the Preparation of Metal Compounds According to the Invention

Example 1

200 ml of an aqueous solution A containing 0.3 mol of Ni and of Cr, in the form of their nitrates $Ni(NO_3)_2.6H_2O$ and $Cr(NO_3)_3.8H_2O$, the Ni/Cr molar ratio being 3, are prepared.

200 ml of an aqueous solution B containing 0.4 mol of sodium carbonate are prepared.

The solution A is gradually run into the solution B over a few minutes, with stirring, the two solutions being at a temperature of 80° C.

The formation of a homogeneous precipitate is observed. The mixture is maintained at 80° C. with stirring for approximately 20 min.

The precipitate is filtered off and washed, on the filter, with 1500 ml of water at 80° C.

The precipitate is then dried in a ventilated oven at 120° C. for 12 h; a green-coloured powder is obtained with the formula: $Ni_6Cr_2(OH)_{16}CO_3.4H_2O$.

This compound is then calcined in a ventilated furnace for 3 h at 300° C. The chemisorbed water and $CO_2$ are thus removed. The precursor of the metal compound according to the invention is composed of a very slightly crystalline mixed oxide of Ni and Cr.

The precursor is then reduced by hydrogen at 350° C. for 29 h. A metal compound according to the invention is obtained which is composed of Ni in the oxidation state 0 and of Cr oxide (Ni/Cr molar ratio=3); this compound is provided in the form of a black powder having a specific surface of 70 $m^2/g$: compound (a).

Examples 2 to 4

Example 1 is repeated, the respective amounts of Ni nitrate and of Cr nitrate being varied, so as to have an Ni/Cr molar ratio of 5 (Example 2), 10 (Example 3) and 20 (Example 4).

After the various stages of the synthesis described in Example 1, the following three metal compounds according to the invention are obtained:

compound (b): black powder composed of Ni and of Cr oxide with an Ni/Cr molar ratio=5, having a specific surface of 103 $m^2/g$;

compound (c): black powder composed of Ni and of Cr oxide with an Ni/Cr molar ratio=10, having a specific surface of 80 $m^2/g$;

compound (d): black powder composed of Ni and of Cr oxide with an Ni/Cr molar ratio=20, having a specific surface of 30 $m^2/g$.

Examples 5 to 10

The amount of copper nitrate $Cu(NO_3)_2.6H_2O$ or of zinc nitrate $Zn(NO_3)_2.6H_2O$ necessary in order to have an Ni/Cu molar ratio of 5, 10 or 20 or an Ni/Zn molar ratio of 5, 10 or 20 is added to the solution A while following the procedure described in Example 1. The Ni+Cu/Cr or Ni+Zn/Cr molar ratio is 5 in all the examples.

After the various stages of the synthesis described in Example 1, the following six metal compounds according to the invention are obtained:

compound (e): black powder composed of Ni, of Cu and of Cr oxide with an Ni/Cu molar ratio=5 and an Ni+Cu/Cr molar ratio=5, having a specific surface of 85 $m^2/g$;

compound (f): black powder composed of Ni, of Cu and of Cr oxide with an Ni/Cu molar ratio=10 and an Ni+Cu/Cr molar ratio=5, having a specific surface of 75 $m^2/g$;

compound (g): black powder composed of Ni, of Cu and of Cr oxide with an Ni/Cu molar ratio=20 and an Ni+Cu/Cr molar ratio=5, having a specific surface of 70 $m^2/g$;

compound (h): black powder composed of Ni, of Zn and of Cr oxide with an Ni/Zn molar ratio=5 and an Ni+Zn/Cr molar ratio=5, having a specific surface of 95 $m^2/g$;

compound (j): black powder composed of Ni, of Zn and of Cr oxide with an Ni/Zn molar ratio=10 and an Ni+Zn/Cr molar ratio=5, having a specific surface of 87 $m^2/g$;

compound (k): black powder composed of Ni, of Zn and of Cr oxide with an Ni/Zn molar ratio=20 and an Ni+Zn/Cr molar ratio=5, having a specific surface of 82 $m^2/g$.

Examples 11 and 12

A solution A is prepared, with the amounts of nickel nitrate $Ni(NO_3)_2.6H_2O$ and of cerium nitrate $Ce(NO_3)_3.6H_2O$ or of Ni nitrate, of chromium nitrate $Cr(NO_3)_3.8H_2O$ and of cerium nitrate necessary in order to have an Ni/Ce molar ratio of 5 or an Ni/Cr+Ce molar ratio of 4, while following the procedure described in Example 1.

After the various stages of the synthesis described in Example 1, the following two metal compounds according to the invention are obtained:

compound (l): black powder composed of Ni and of Cr oxide with an Ni/Ce molar ratio=5, having a specific surface of 100 $m^2/g$;

compound (m): black powder composed of Ni, of Ce oxide and of Cr oxide with an Ni/Ce+Cr molar ratio=4 and a Cr/Ce molar ratio=5, having a specific surface of 90 $m^2/g$.

Examples of the Use of Metal Compounds Acording to the Invention as Hydrogenation Catalysts Examples 13 to 22 and Comparative Test 1

Various metal compounds prepared above are tested as catalysts.

The hydrogenation test makes it possible, under well-determined conditions, to compare the activity and the selectivity of metal compounds of various compositions.

The equipment used consists of a stainless steel autoclave in which the reaction is carried out, the said autoclave being equipped with a pressure-resistant steel dropping funnel, a hydrogen or inert gas inlet, a self-regulating heating system, means for measuring and controlling the pressure and temperature, a magnetic bar rotating at 1500 revolutions/minute and an outlet for the gases.

The metal compound according to the invention (0.2 g of Ni) with either (1) 40 g of ethanol and 1 6 g of water (Examples 13 to 16 and Comparative Test 1) or (2) 0.3 ml of ethanol, 38 g of hexamethylenediamine and 4 g of distilled water (Examples 17 to 22) and the alkali metal hydroxide (sodium hydroxide, except when otherwise mentioned), in a proportion of 2 mol/kg of Ni of the metal compound, are charged to the autoclave. The mixture is homogenized and is covered with argon. Purging is then carried out with nitrogen and then with hydrogen. Heating is then carried out to the chosen temperature (80° C.) and the chosen pressure (25 bar) is established.

1 g of adiponitrile (AdN) is introduced into the dropping funnel and the latter is purged three times with hydrogen. Injection of the AdN is carried out over 1 h.

By way of comparison, a test is carried out under the same conditions as Examples 13 to 16 with the solvent medium (1), use being made of a Raney nickel containing 4.5% of Cr confirmed that the by-products are, taken as a whole, all identified.

The selectivities towards each of the by-products are represented by the molar percentage of the by-product formed with respect to the converted AdN. In all the Examples and Comparative Tests carried out, the degree of conversion of the AdN (and that of the intermediate aminocapronitrile) is 100%. The selectivities are expressed, for convenience, in $\mu$mol of by-product per mole of converted AdN.

The reference of the metal compound used, the nature of the divalent metals and doping metals of which it is composed, the molar ratio of these metals and the selectivities determined towards HMD and towards by-products are shown in Table 1 below.

TABLE 1

| Example | Catalyst | Metal M used in combination with the divalent metal | Ni + M/Cr | Ni/M | S % HMD | S HMI | S AMCPA | S NEtHMD | S DCH | S BHT |
|---|---|---|---|---|---|---|---|---|---|---|
| Ex. 13 | a | none | 3 | — | 99.3 | 200 | 150 | 1650 | 750 | 4000 |
| Ex. 14 | b | none | 5 | — | 99.4 | 250 | 100 | 1600 | 750 | 2900 |
| Ex. 15 | c | none | 10 | — | 99.6 | 450 | 100 | 1350 | 700 | 1250 |
| Ex. 16 | d | none | 20 | — | 99.7 | 150 | 150 | 1550 | 1000 | 300 |
| Ex. 17 | e | Cu | 5 | 5 | 98.7 | 900 | 1400 | 1300 | 400 | 8500 |
| Ex. 18 | f | Cu | 5 | 10 | 98.9 | 1150 | 1100 | 1350 | 450 | 7850 |
| Ex. 19 | g | Cu | s | 20 | 99.6 | 550 | 450 | 850 | 650 | 2650 |
| Ex. 20 | h | Zn | 5 | 5 | 99.4 | 500 | 900 | 1300 | 600 | 2100 |
| Ex. 21 | j | Zn | 5 | 10 | 99.4 | 300 | 450 | 1300 | 1000 | 2300 |
| Ex. 22 | k | Zn | 5 | 20 | 99.4 | 300 | 450 | 1300 | 1000 | 2300 |
| CT 1 | Raney Ni | none | 20 | — | 98.2 | 1100 | 2300 | 3500 | 1400 | 9000 | and having a specific surface of 70 m$^2$/g (Ni/Cr molar ratio of approximately 20). This Raney nickel contains approximately 7% by weight of Al metal with respect to the Ni.

At the end of the injection, the autoclave is left at the temperature and the pressure until hydrogen consumption has ceased. The hydrogenate is quantitatively determined by vapour phase chromatography. The selectivities (S) of the various by-products obtained are thus determined.

The by-products which are quantitatively determined are as follows:

EMI: Rexamethyleneimine

AMCPA: Aminomethylcyclopentylamine

NEtMMD: N-Ethylhexamethylenediamine

DCH: cis and trans Diaminocyclohexane

BHT: Bis(hexamethylene)triamine.

The selectivity towards EMD in percentage is given by the relationship: 100−sum of the selectivities of the by-products. In fact, as most of the reaction solvent is composed of HMD, it cannot be directly quantitatively determined in a very precise way. In contrast, it has been Examples 23 and 24

Examples 17 to 22, for the hydrogenation of AdN, are repeated under the same operating conditions and with the solvent medium (2), while using the metal compounds (1) and (m) as catalysts.

The results collated in Table 2 below are obtained.

TABLE 2

|  | Example 23/Compound (1) | Example 24/Compound (m) |
|---|---|---|
| S % HMD | 99.0 | 99.0 |
| S HMI | 900 | 550 |
| S AMCPA | 3000 | 300 |
| S NEtHMD | 1250 | 550 |
| S DCH | 400 | 500 |
| S BHT | 3400 | 7600 |

Comparative Test 2

Preparation of a metal compound not included within the invention: Ni/Al$_2$O$_3$ A solution A is prepared, with the amounts of nickel nitrate Ni(NO$_3$)$_2$.6H$_2$O and of aluminium nitrate Al(NO$_3$)$_3$.8H$_2$O necessary in order to have an Ni/Al molar ratio of 3, while following the procedure described in Example 1.

After the various stages of the synthesis described in Example 1, the following metal compound is obtained:

compound (p): black powder composed of Ni and of Al oxide with an Ni/Al molar ratio=3, having a specific surface of 150 m$^2$/g.

Comparative Test 3

Use of the metal compound (p) as hydrogenation catalyst.

Examples 13 to 16, for the hydrogenation of AdN, are repeated under the same operating conditions and with the solvent medium (1), while using the metal compound (p) as catalyst.

The following results are obtained:

| | |
|---|---|
| S % HMD | 81.3 |
| S HMI | 154,000 |
| S AMCPA | 0 |
| S NEtHMD | 2500 |
| S DCH | 420 |
| S BHT | 15,300 |
| S ACA* and CVA* | 15,000 |

(*) ACA = aminocaproamide; CVA = cyanovaleramide

Example 25 and Comparative Test 4

Ageing of the catalyst in a hydrogenation reaction.

A series of hydrogenations of AdN is carried out under the operating conditions described for Examples 13 to 22 with the medium (2) but injecting 10 g of AdN over 1 h, on the one hand with the compound (d) according to the invention (Ni/Cr=20) and, on the other hand, with the Raney nickel used in Comparative Test 1 (Ni/Cr=20).

The completion time Ct1 for each hydrogenation is measured, that is to say the time during which absorption of hydrogen continues, after the end of injection of the AdN.

A second injection of 10 g of AdN is carried out over 1 h with each of the two catalysts and the completion time Ct2 is measured.

The following results are obtained:

Example 25
Ct1=15 min (S HMD=99%)
Ct2=16 min

Comparative Test 4
Ct1=17 min (S HMD=98.7%)
Ct2=99 min

A rapid deactivation of the Raney catalyst is observed whereas the catalyst of the invention retains a constant activity.

We claim:

1. Process for nitrile hydrogenation, comprising carrying out in the presence of a catalyst chosen from metal compounds containing one or a number of divalent metals, chosen from nickel and cobalt, at least partially in the reduced state, bulked by a phase comprising one or a number of doping metals chosen from chromium, molybdenum, iron, manganese, titanium, vanadium, gallium, indium, bismuth, yttrium, cerium, lanthanum and the other trivalent lanthanides, in the form of oxides, the doping metal/divalent metal molar ratio being between 0.01 and 0.50.

2. Process according to claim 1, wherein the nitrile is chosen from aliphatic, cycloaliphatic, heterocyclic or aromatic mononitriles or dinitriles.

3. Process according to claim 1, wherein the nitrile is chosen from the nitrile substances of formula (II):

$$NC\text{---}R\text{---}CN \qquad (II)$$

in which R represents a linear or branched alkylene or alkenylene group having from 1 to 12 carbon atoms or an unsubstituted or substituted arylene or aralkylene or aralkenylene group.

4. Process according to claim 1, wherein at least 20% of the atoms of the divalent metals are in the reduced state.

5. Process according to claim 1, wherein the divalent metals are provided in the form of particles having sizes lying between 1 and 20 nanometers.

6. Process according to claim 1, wherein the doping metal/divalent metal molar ratio is between 0.05 and 0.30.

7. Process according to claim 1, wherein from 0% to 50%, in moles per mole, of the divalent metals, nickel or cobalt, are substituted by one or a number of other metals chosen from zinc, copper, silver, gold, ruthenium, platinum and palladium.

8. Process according to claim 1, wherein from 0% to 50%, in moles per mole, of the doping metal oxides are substituted by aluminum oxide.

9. Process according to one of claims 1 to 8, characterized in that from 0% to 50%, in moles per mole, of the doping metal oxides are substituted by aluminium oxide.

10. Process according to claim 3 wherein R represents a linear or branched alkylene radical having from 1 to 6 carbon atoms.

11. Process according to claim 4, wherein at least 50% of the atoms of the divalent metals are in the reduced state.

12. Process according to claim 5, wherein the divalent metals are provided in the form of particles having sizes lying between 1 and 20 nanometers.

* * * * *